(12) United States Patent
Jordison et al.

(10) Patent No.: US 12,312,557 B2
(45) Date of Patent: May 27, 2025

(54) METHODS OF MAKING ANTIMICROBIAL COMPOSITIONS AND/OR VIRUCIDAL DISINFECTANT COMPOSITIONS FROM VEGETABLE OIL, AND RELATED ANTIMICROBIAL COMPOSITIONS AND/OR VIRUCIDAL DISINFECTANT COMPOSITIONS AND USES

(71) Applicant: POET Research, Inc., Sioux Falls, SD (US)

(72) Inventors: Tyler L. Jordison, Fort Dodge, IA (US); Melanie A. Eichmann, Canistota, SD (US); Steven T. Bly, Sioux Falls, SD (US); Benjamin P. Gacke, Baltic, SD (US); Andrew J. Manning, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 556 days.

(21) Appl. No.: 17/403,086

(22) Filed: Aug. 16, 2021

(65) Prior Publication Data
US 2022/0049181 A1 Feb. 17, 2022

Related U.S. Application Data

(60) Provisional application No. 63/066,586, filed on Aug. 17, 2020.

(51) Int. Cl.
| | | |
|---|---|---|
| *C11B 3/02* | (2006.01) | |
| *A01N 37/04* | (2006.01) | |
| *A01N 37/06* | (2006.01) | |
| *A01N 37/42* | (2006.01) | |
| *A23B 2/754* | (2025.01) | |

(52) U.S. Cl.
CPC ............... *C11B 3/02* (2013.01); *A01N 37/04* (2013.01); *A01N 37/06* (2013.01); *A01N 37/42* (2013.01); *A23B 2/754* (2025.01)

(58) Field of Classification Search
CPC ........... C11B 3/02; A01N 37/04; A01N 37/06; A01N 37/42; A01N 37/16; A01N 61/00; A01N 65/00; A23L 3/3508; Y02A 40/90; Y02P 60/87; A01P 1/00; A23K 10/38; A23K 50/10; A23K 50/30; A23K 50/75; A61L 2/183
See application file for complete search history.

(56) References Cited

U.S. PATENT DOCUMENTS

| | | |
|---|---|---|
| 2,083,572 A | 6/1937 | McKee |
| 2,865,937 A | 12/1958 | Maggiolo |
| 3,219,675 A | 11/1965 | Seekircher |
| 3,246,008 A | 4/1966 | Evans et al. |
| 4,185,025 A | 1/1980 | Carduck et al. |
| 4,613,694 A | 9/1986 | Rossi et al. |
| 8,008,516 B2 | 8/2011 | Cantrell et al. |
| 8,702,819 B2 | 4/2014 | Bootsma |
| 9,061,987 B2 | 6/2015 | Bootsma |
| 9,695,449 B2 | 7/2017 | Bootsma |
| 9,885,006 B2 | 2/2018 | Samsodin et al. |
| 9,896,643 B2 | 2/2018 | Redford |
| 10,711,221 B2 | 7/2020 | Lamprecht et al. |
| 10,851,327 B2 | 12/2020 | Urban et al. |
| 2003/0070691 A1* | 4/2003 | Giletto ............... A01N 59/00 510/382 |
| 2005/0010069 A1* | 1/2005 | Fitchett ............... C08L 59/00 568/959 |
| 2010/0233823 A1 | 9/2010 | Schemmer |
| 2019/0075825 A1 | 3/2019 | Dasari et al. |
| 2020/0339910 A1 | 10/2020 | Lamprecht et al. |
| 2021/0002584 A1 | 1/2021 | Urban et al. |
| 2021/0032564 A1 | 2/2021 | Urban et al. |

FOREIGN PATENT DOCUMENTS

| | | |
|---|---|---|
| DE | 2713863 A1 | 10/1978 |
| WO | 03085072 A1 | 10/2003 |
| WO | 2012168770 A1 | 12/2012 |
| WO | 2019157334 A1 | 8/2019 |
| WO | 2019241269 A1 | 12/2019 |

OTHER PUBLICATIONS

S. Moureu et al., "Ozonation of sunflower oils: Impact of experimental conditions on the composition and the antibacterial activity of ozonized oils," Chemistry and Physics of Lipids 186 (2015) 79-85.*
Huang et al., "Short- and medium-chain fatty acids exhibit antimicrobial activity for oral microorganisms," Arch Oral Biol., 56(7), pp. 650-654, Jul. 2011, (8 pages).
ZeniPRO™ brand, "Liquid Mold Inhibitor," Kemin Product Specifications, 2019, retrieved from 'https://www.kemin.com/na/en-ca/markets/animal/products/zenipro' (1 page).
ZeniPRO™ brand, "A liquid mold inhibitor for wet distillers grains.," Kemin, retrieved from 'https://www.kemin.com/na/en-ca/markets/animal/products/zenipro', on Dec. 15, 2023, (4 pages).
Breathnach, "Azelaic acid: potential as a general antitumoural agent", Medical Hypotheses, 52(3), pp. 221-226, 1999, (6 pages).

(Continued)

*Primary Examiner* — Monica A Shin
(74) *Attorney, Agent, or Firm* — Kagan Binder, PLLC

(57) ABSTRACT

The present disclosure relates to methods and systems for making one or more antimicrobial compositions and/or one or more virucidal disinfectant compositions. Said methods and systems include exposing a vegetable oil composition to ozone gas to cause ozonolysis of on one or more unsaturated fatty acids present in the vegetable oil composition, thereby forming an ozonated vegetable oil composition and exposing the ozonated vegetable oil composition to a temperature greater than 60° C. while in contact with water to decompose one or more ozonide compounds and form a heat-treated, ozonated vegetable oil composition. The present disclosure also relates to one or more uses of said one or more antimicrobial compositions and/or one or more virucidal disinfectant compositions.

20 Claims, 4 Drawing Sheets

(56) References Cited

OTHER PUBLICATIONS

Nepotchatykh et al., "Degradation of Dicarboxylic Acids (C2—C9) upon Liquid-Phase Reactions with O3 and Its Atmospheric Implications", Environmental Science & Technology, vol. 36, No. 15, pp. 3265-3269, 2002, (6 pages).

Ionidis et al., "Development and virucidal activity of a novel alcohol-based hand disinfectant supplemented with urea and citric acid", BMC Infectious Diseases, 16:77, 2016, (10 pages).

Grego et al., "Dicarboxylic acids, an alternate fuel substrate in parenteral nutrition: an update", Clinical Nutrition, vol. 14, pp. 143-148, 1995, (6 pages).

Turner et al., "Effectiveness of Hand Sanitizers with and without Organic Acids for Removal of Rhinovirus from Hands", Antimicrobial Agents and Chemotherapy, vol. 54, No. 3, pp. 1363-1364, 2010, (2 pages).

Turner et al., "Efficacy of Organic Acids in Hand Cleansers for Prevention of Rhinovirus Infections", Antimicrobial Agents and Chemotherapy, vol. 48, No. 7, pp. 2595-2598, 2004, (4 pages).

Passi et al., "Metabolism of straight saturated medium chain length (C9 to C12) dicarboxylic acids", Journal of Lipid Research, vol. 24, pp. 1140-1147, 1983, (9 pages).

Long et al., "Mixed organic acids as antibiotic substitutes improve performance, serum immunity, intestinal morphology and microbiota for weaned piglets", Animal Feed Science and Technology, vol. 235, pp. 23-32, 2018, (10 pages).

Omonov et al., "Ozonolysis of Canola Oil: A Study of Product Yields and Ozonolysis Kinetics in Different Solvent Systems", Journal of the American Oil Chemists' Society, vol. 88, pp. 689-705, 2011, (18 pages).

Mingrone et al., "Preliminary Studies of a Dicarboxylic Acid as an Energy Substrate in Man", Journal of Parenteral and Enteral Nutrition, vol. 13, No. 3, pp. 299-305, 1989, (7 pages).

Tacchino et al., "Short-Term Infusion of Azelaic vs Intralipid in Healthy Subjects Evaluated by Indirect Calorimetry", Journal of Parenteral and Enteral Nutrition, vol. 14, No. 2, pp. 169-172, 1990, (4 pages).

Lai et al., "The effects of dietary medium-chain triacylglycerols on growth performance and intestinal microflora in young pigs", Journal of Animal and Feed Sciences, vol. 23, pp. 331-336, 2014, (6 pages).

Poli et al., "Virucidal Activity of Organic Acids", Food Chemistry, vol. 4, Issue 4, pp. 251-258, 1978, (8 pages).

* cited by examiner

METHODS OF MAKING ANTIMICROBIAL COMPOSITIONS AND/OR VIRUCIDAL DISINFECTANT COMPOSITIONS FROM VEGETABLE OIL, AND RELATED ANTIMICROBIAL COMPOSITIONS AND/OR VIRUCIDAL DISINFECTANT COMPOSITIONS AND USES

CROSS-REFERENCE TO RELATED APPLICATION

The present nonprovisional patent application claims the benefit of commonly owned provisional Application having Ser. No. 63/066,586, filed on Aug. 17, 2020, wherein the entirety of said provisional application is incorporated herein by reference.

BACKGROUND

The present disclosure relates to biorefineries and co-products made therefrom. An example of such biorefinery is an ethanol biorefinery. Ethanol biorefineries typically produce fuel-grade ethanol using a fermentation-based process. Much of the ethanol used for transportation fuel in the United States is produced from the fermentation of corn. In an exemplary dry-grind ethanol production process, a vegetable such as corn is delivered to a biorefinery and its particle size can be reduced by grinding the corn in a dry milling step. The resulting corn flour can then be combined with water, nutrients, enzymes, yeast, and/or other ingredients in a fermenter. Enzymes can convert starch into fermentable sugars. Yeast converts fermentable sugars into ethanol. Fermentation results in a beer stream that includes, e.g., ethanol, water, suspended solids, dissolved solids, and corn oil. The beer stream is processed by a distillation unit where ethanol is removed. The stream from the distillation unit after ethanol has been recovered is referred to as whole stillage. This whole stillage stream includes, e.g., suspended solids, dissolved solids, water, and corn oil. The whole stillage stream is separated, typically by decanting centrifuges, into a thin stillage stream and a wet cake stream. The wet cake stream has a higher concentration of solids than whole stillage and is typically of a relatively high viscosity sludge-like consistency. The thin stillage has a lower concentration of suspended solids than whole stillage and is typically of a relatively low viscosity liquid stream. The solids concentration of the thin stillage stream can be increased in an evaporation step where water is evaporated from the thin stillage. Concentrated thin stillage is referred to as syrup in the art. The syrup stream contains an increased concentration of corn oil, which can be separated and sold as distiller's corn oil (DCO). Alternatively, corn oil can be separated one or more points upstream and/or downstream in a biorefinery. For example, prior to fermentation, from the beer, from whole stillage, from thin stillage, from wet cake or any other corn oil containing process stream.

Biorefineries may separate DCO from process streams using centrifuges to produce a corn oil product. For example, U.S. Pat. No. 9,061,987 (Bootsma), U.S. Pat. No. 8,702,819 (Bootsma), and U.S. Pat. No. 9,695,449 (Bootsma), describe the separation of DCO using centrifuges, wherein the entireties of said patents are incorporated herein by reference. U.S. Pat. No. 8,008,516 (Cantrell et al.) describes DCO separation from thin stillage, wherein the entirety of said patent is incorporated herein by reference. U.S. Pat. No. 9,896,643 (Redford) reports methods and systems for recovering a desired co-product from a feedstock to ethanol production process, wherein the entirety of said patent is incorporated herein by reference.

While DCO is a valuable co-product, it is typically sold at commodity prices and used as a feedstock for biodiesel production or as an animal feed ingredient.

There is a continuing need for processing vegetable oil compositions from a biorefinery to provide different compositions for a wide variety of uses.

SUMMARY

The present disclosure includes embodiments of a method of making one or more antimicrobial compositions and/or one or more virucidal disinfectant compositions, wherein the method includes:
a) exposing a vegetable oil composition to ozone gas to cause ozonolysis of on one or more unsaturated fatty acids present in the vegetable oil composition, thereby forming an ozonated vegetable oil composition, wherein the ozonated vegetable oil composition includes one or more ozonide compounds;
b) exposing the ozonated vegetable oil composition to a temperature greater than 60° C. while in contact with water to decompose one or more ozonide compounds and form a heat-treated, ozonated vegetable oil composition including a carboxylic acid chosen from a C1 carboxylic acid, a C2 carboxylic acid, a C3 carboxylic acid, a C4 carboxylic acid, and mixtures thereof, wherein the heat-treated, ozonated vegetable oil composition includes an aqueous phase and an oil phase; and
c) separating at least a portion of the aqueous phase from the heat-treated, ozonated vegetable oil composition, wherein the at least a portion of the aqueous phase from the heat-treated, ozonated vegetable oil composition is an antimicrobial composition and/or virucidal disinfectant composition including a carboxylic acid chosen from a C1 carboxylic acid, a C2 carboxylic acid, a C3 carboxylic acid, a C4 carboxylic acid, and mixtures thereof.

The present disclosure also includes embodiments of a method of making one or more antimicrobial compositions and/or one or more virucidal disinfectant compositions, wherein the method includes:
a) exposing a vegetable oil composition to ozone gas to cause ozonolysis of on one or more unsaturated fatty acids present in the vegetable oil composition, thereby forming an ozonated vegetable oil composition, wherein the ozonated vegetable oil composition includes one or more ozonide compounds;
b) exposing the ozonated vegetable oil composition to a temperature of 60° C. or greater while in contact with water to decompose one or more ozonide compounds via a decomposition reaction and form a heat-treated, ozonated vegetable oil composition, wherein the heat-treated, ozonated vegetable oil composition includes an aqueous phase and an oil phase, and wherein at least step "b" does not occur in the presence of an exogenous amount of organic solvent that is a product of the decomposition reaction; and
c) separating at least a portion of the aqueous phase from the heat-treated, ozonated vegetable oil composition, wherein the at least a portion of the aqueous phase from the heat-treated, ozonated vegetable oil composition is an antimicrobial composition and/or a virucidal disinfectant composition.

The present disclosure also includes embodiments of a biorefinery including:

a) a source of vegetable oil composition; and
b) a system in fluid communication with a source of ozone gas and the vegetable oil composition, wherein the system is configured to:
  i) expose the vegetable oil composition to ozone gas to cause ozonolysis of on one or more unsaturated fatty acids present in the vegetable oil composition, thereby forming an ozonated vegetable oil composition including one or more ozonide compounds;
  ii) expose the ozonated vegetable oil composition to a temperature greater than 60° C. while in contact with water to decompose one or more ozonide compounds and form a heat-treated, ozonated vegetable oil composition including a carboxylic acid chosen from a C1 carboxylic acid, a C2 carboxylic acid, a C3 carboxylic acid, a C4 carboxylic acid, and mixtures thereof, wherein the heat-treated, ozonated vegetable oil composition includes an aqueous phase and an oil phase and/or to expose the ozonated vegetable oil composition to a temperature of 60° C. or greater while in contact with water to decompose one or more ozonide compounds via a decomposition reaction and form a heat-treated, ozonated vegetable oil composition, wherein the heat-treated, ozonated vegetable oil composition includes an aqueous phase and an oil phase, and wherein at least does exposing the ozonated vegetable oil composition to a temperature of 60° C. or greater while in contact with water does not occur in the presence of an exogenous amount of organic solvent that is a product of the decomposition reaction; and
  iii) to separate at least a portion of the aqueous phase from the heat-treated, ozonated vegetable oil composition.

BRIEF DESCRIPTION OF THE DRAWINGS

FIGS. 1A-4B show photographs of each wet cake sample from Example 2 at 0 days and 7 days at ambient conditions.

DETAILED DESCRIPTION

Figures 1A, 1B:
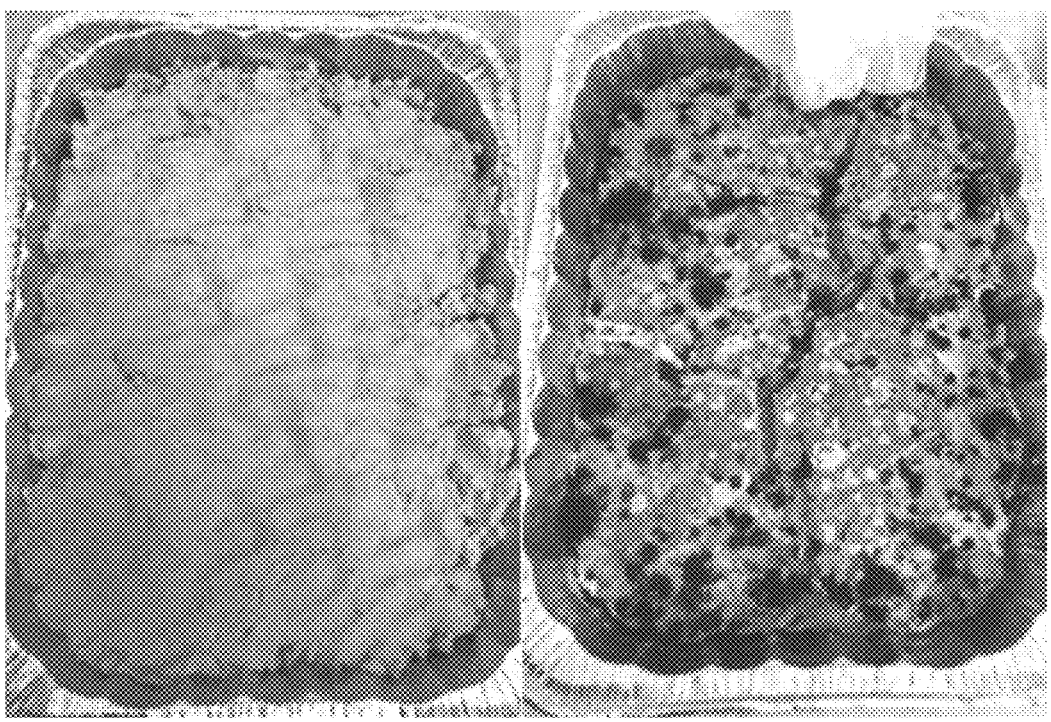

Methods of Making Antimicrobial Compositions and/or Virucidal Disinfectant Compositions The present disclosure includes embodiments of methods of making one or more antimicrobial compositions and/or one or more virucidal disinfectant compositions.

Vegetable Oil Composition

Embodiments of the present disclosure can use a wide variety of vegetable oil compositions as feedstock for forming one or more antimicrobial compositions and/or one or more virucidal disinfectant compositions according to the present disclosure.

As used herein, a "vegetable oil composition" refers to a composition that has a vegetable oil component and that can be processed as described herein to form an antimicrobial composition and/or a virucidal disinfectant composition. In some embodiments, a vegetable oil composition can include oil derived from a plant material (e.g., grain), oleaginous microorganisms, and the like.

Non-limiting examples of a vegetable oil component can be chosen from corn oil, soybean oil, rapeseed oil, sunflower oil, olive oil, castor bean oil, wheat germ oil, sorghum oil, rice bran oil, barley oil, oat oil, millet see oil, rye oil, combinations thereof, and the like.

A vegetable oil composition can include a triglyceride component, a diglyceride component and/or a monoglyceride component. In some embodiments, a vegetable oil composition can include a triglyceride component in an amount of at least 70 percent by weight of the total vegetable oil composition, at least 80 percent by weight of the total vegetable oil composition, at least 90 percent by weight of the total vegetable oil composition, or even at least 95 percent by weight of the total vegetable oil composition.

A vegetable oil composition can be a single phase (e.g., oil phase) that includes the vegetable oil component as substantially all of the phase with minor amounts of other components. In some embodiments, a vegetable oil composition can include an aqueous phase before or during ozonation. The aqueous phase can be in a variety of forms such as a solution of water soluble components (e.g., carboxylic acids), an emulsion of water and part of the vegetable oil component, and the like.

As described below, a vegetable oil composition that includes an aqueous phase can help with ozonation and/or any subsequent heat treatment. In addition, as described below, an aqueous phase can be recovered from an ozonated vegetable oil composition to form at least one antimicrobial composition according to the present disclosure. In some embodiments, a vegetable oil composition includes a weight ratio of vegetable oil component to water in the range from 1:0.1 to 1:0.9, from 1:0.1 to 1:0.5, from 1:1 to 1:10, from 1:1 to 1:5, or even from 1:1 to 1:3. An aqueous composition such a biorefinery process stream (e.g., thin stillage, process water, and the like) can be combined with a vegetable oil composition at one or more points in a process according to the present disclosure. For example, an aqueous composition can be combined in one or more amounts with a vegetable oil composition prior to, during, and/or after ozonolysis (discussed below), and/or prior to, during, and/or after heat-treating the ozonated, vegetable oil composition (discussed below). An example of one or more such biorefinery process stream is described in U.S. Pat. No. 10,851,327 (Urban et al.), wherein the entirety of said patent is incorporated herein by reference.

A vegetable oil composition to be used as a feedstock in process according to the present disclosure can be obtained from variety of sources. In some embodiments, a vegetable oil composition can be derived from one or more process streams in a biorefinery. Non-limiting examples process streams in a biorefinery include a fermentation product stream that has been produced via fermentation of a vegetable material, a whole stillage stream and/or a stream derived from whole stillage such as thin stillage, syrup, oil emulsion, oil product (e.g., distiller's corn oil (DCO)) and the like. In some embodiments, one or more such process streams can be concentrated, diluted, or combined (mixed) with one or more biorefinery process streams to provide a vegetable oil composition having a weight ratio of vegetable oil component to water as described above. For example, at least one process stream that includes vegetable oil component (e.g., a stillage stream such as whole stillage, thin stillage, syrup, oil emulsion, oil product (e.g., distiller's corn oil (DCO)), and the like) and at least one process stream that includes an aqueous component (e.g., a stillage stream such as whole stillage, backset, recycled process water, thin stillage, syrup, oil emulsion, make-up water (e.g., fresh make-up water) and the like)) can be combined (mixed) together to form a vegetable oil composition. In some embodiments, the combined streams can be concentrated or diluted as desired (e.g., to provide a vegetable oil composition having a weight ratio of vegetable oil component to water as described above).

Ozonolysis

A vegetable oil composition can be exposed to an ozone gas to cause ozonolysis of on one or more unsaturated fatty acids present in the vegetable oil composition, thereby forming what is referred to herein as an "ozonated" vegetable oil composition. As used herein, "ozonolysis" means the cleavage of unsaturated bonds of alkene, alkyne, and/or azo compounds by reaction with ozone. A vegetable oil composition can be exposed to an ozone gas under conditions that cause at least partial ozonolysis of fatty acid present in glyceride (monoglyceride, diglyceride, and/or triglyceride) of the vegetable oil component, which can form an ozonated vegetable oil composition that includes a variety of reaction products. Such reaction products can include relatively unstable ozonide compounds. In some embodiments, as discussed below, the ozonated vegetable oil composition can be exposed to a heat treatment to decompose the ozonides into one or more aldehydes and/or one or more carboxylic acids.

Ozone gas can be exposed to a vegetable oil composition in one or more of a variety of ways to cause ozonolysis as described herein. For example, an ozone gas can be introduced into the headspace of a closed vessel so that the ozone gas diffuses into the vegetable oil composition. As another example, ozone gas can be sparged into the vegetable oil composition so that the gas bubbles including ozone gas transfer into (e.g., up and through) the vegetable oil composition. As another example, falling film techniques can be used to contact a vegetable oil composition with an ozone gas to cause ozonolysis of the vegetable oil composition as desired. For example, a vegetable oil composition can be caused to flow over a weir in an atmosphere of ozone gas. As another example, a flow of ozone gas can be caused to contact a flow of the vegetable oil composition in a countercurrent manner.

Contacting a vegetable oil composition with ozone gas as described herein may change the color the vegetable oil composition. For example, contacting a vegetable oil composition with ozone gas as described herein may lighten ("bleach") the vegetable oil composition.

Optionally, the vegetable oil composition can be agitated or mixed to facilitate transferring ozone gas into and throughout the vegetable oil composition so as to achieve the desired ozonolysis results. For example, a continuous stirred tank reactor (CSTR) can be used to agitate or mix the vegetable oil composition. The speed of the stirring mechanism (rpms) can be adjusted based on a variety of factors such as tank size, viscosity, and the like.

A flowrate of ozone gas can be selected for introduction into a volume of vegetable oil composition to contact the vegetable oil composition in a variety of ways to cause ozonolysis of the vegetable oil composition and form an ozonated vegetable oil composition as described herein. In some embodiments, a ratio of volumetric flow of ozone gas to volume of vegetable oil composition can be from 0.5 to 10 lpm of ozone gas per liter of vegetable oil composition; from 0.75 to 9 lpm of ozone gas per liter of vegetable oil composition; from 1 to 8 lpm of ozone gas per liter of vegetable oil composition; from greater than 0 to 5 lpm of ozone gas per liter of vegetable oil composition; or even 1.5 to 7 lpm of ozone gas per liter of vegetable oil composition. A flow of ozone gas can have a range of temperatures and pressures. In some embodiments, the flow of ozone gas can have a temperature from 0° C. to 50° C. and a pressure up to 50 psi.

A vegetable oil composition can be exposed to ozone gas for a time period to cause ozonolysis and form an ozonated vegetable oil composition. The time period selected can depend on a variety of factors such as temperature during exposure to the ozone gas and/or the ratio of ozone gas volumetric flowrate to volume of vegetable oil composition, and the like. In some embodiments, a vegetable oil composition can be exposed to ozone gas for a time period from 1 minute to 20 hours, from 30 minutes to 15 hours, from 1 hour to 15 hours, from 4 hours to 15 hours, from 4 hours to 10 hours, or even from 1 hour to 5 hours.

Ozonation of the vegetable oil composition can be performed under a variety of additional conditions to form an ozonated vegetable oil composition depending on one or more factors such controlling the ozonolysis reaction to provide a target compositional profile of an ozonated vegetable oil composition having desirable antimicrobial and/or virucidal disinfectant, providing desirable processing properties (e.g., viscosity), and the like.

Ozonolysis of the vegetable oil composition is an exothermic reaction so controlling the temperature of the vegetable oil composition at least while it is exposed to ozone gas can prevent a thermal "runaway" due to reaction. Temperature of the vegetable oil composition can be controlled using one or more of a variety of techniques such as including water in the vegetable oil composition, heat exchangers, combinations thereof, and the like. In some embodiments, temperature control during ozonolysis can be provided by passing tap water (e.g., water at a temperature from 15° C. to 25° C.) through a heat exchanger to absorb the heat or reaction due to ozonolysis.

In some embodiments, a vegetable oil composition can be exposed to ozone gas in the presence of water by mixing added (exogenous) water with the vegetable oil composition prior to and/or during ozonolysis to help manage the temperature of the vegetable oil composition and absorb heat from the ozonolysis reactions.

Including added water in the vegetable oil composition during ozonolysis is also advantageous because the water present in the aqueous phase can help partition water-soluble components such as aldehydes and/or carboxylic acids that may be formed (e.g., during subsequent heat treatment described below) into the aqueous phase, which can be recovered to form an antimicrobial composition and/or virucidal disinfectant composition, as discussed below.

Alternatively, a vegetable oil composition can have no added water present during ozonation and, thus, include a relatively low amount of moisture content during ozonation (e.g., from 0.1 to 1 percent, or even from 0.1 to 0.5 percent by weight of the total vegetable oil composition).

A vegetable oil composition can be exposed to a temperature while being exposed to an ozone gas to facilitate ozonolysis and form an ozonated vegetable oil composition according to the present disclosure. In some embodiments, a vegetable oil composition can be exposed to ozone gas while the vegetable oil composition is maintained at a temperature from greater than 0° C. to less than 60° C., from greater than 0° C. to 50° C., from greater than 0° C. to 20° C. from 1° C. to 10° C., or even from 2° C. to 8° C. A vegetable oil composition can be exposed to a pressure while being exposed to an ozone gas to facilitate ozonolysis and form an ozonated vegetable oil composition according to the present disclosure. In some embodiments, a vegetable oil composition can be exposed to ozone gas while the vegetable oil composition is exposed to a vacuum, at atmospheric pressure, or at a pressure greater than atmospheric pressure.

A vegetable oil composition can be exposed to ozone gas via a batch process, a continuous process, or a combination of multiple batch processes in communication with a continuous process so that the overall process operates on a continuous basis. In some embodiments, methods of forming an antimicrobial composition and/or a virucidal disinfectant composition, including exposing a vegetable oil composition to ozone gas can be integrated in an existing biorefinery (e.g., a corn to ethanol biorefinery) or as a stand-alone facility. For example, a portion of one or more process streams in a biorefinery could be diverted from the main process and processed according to the present disclosure to form one or more antimicrobial compositions and/or a virucidal disinfectant compositions.

For illustration purposes, it is noted that corn oil has a relatively high degree of unsaturated fatty acids, which tend to react rapidly with ozone according to the Criegee mechanism. In the Criegee mechanism, ozonides are first formed, and then these ozonides decompose to aldehydes and carboxylic acids when exposed to an appropriate temperature for a sufficient amount of time (e.g., after being heat-treated as explained further below). The primary reacting molecules in corn oil ozonolysis are linoleic acid (~55-58 wt % of the oil) and oleic acid (~25-28 wt % of the oil). These unsaturated fatty acids are oxidatively cleaved at the double bonds to form a triglyceride of azelaic acid and C3, C6, and C9 aldehydes/carboxylic acids according to the following reactions showing the reaction products of the ozonolysis:

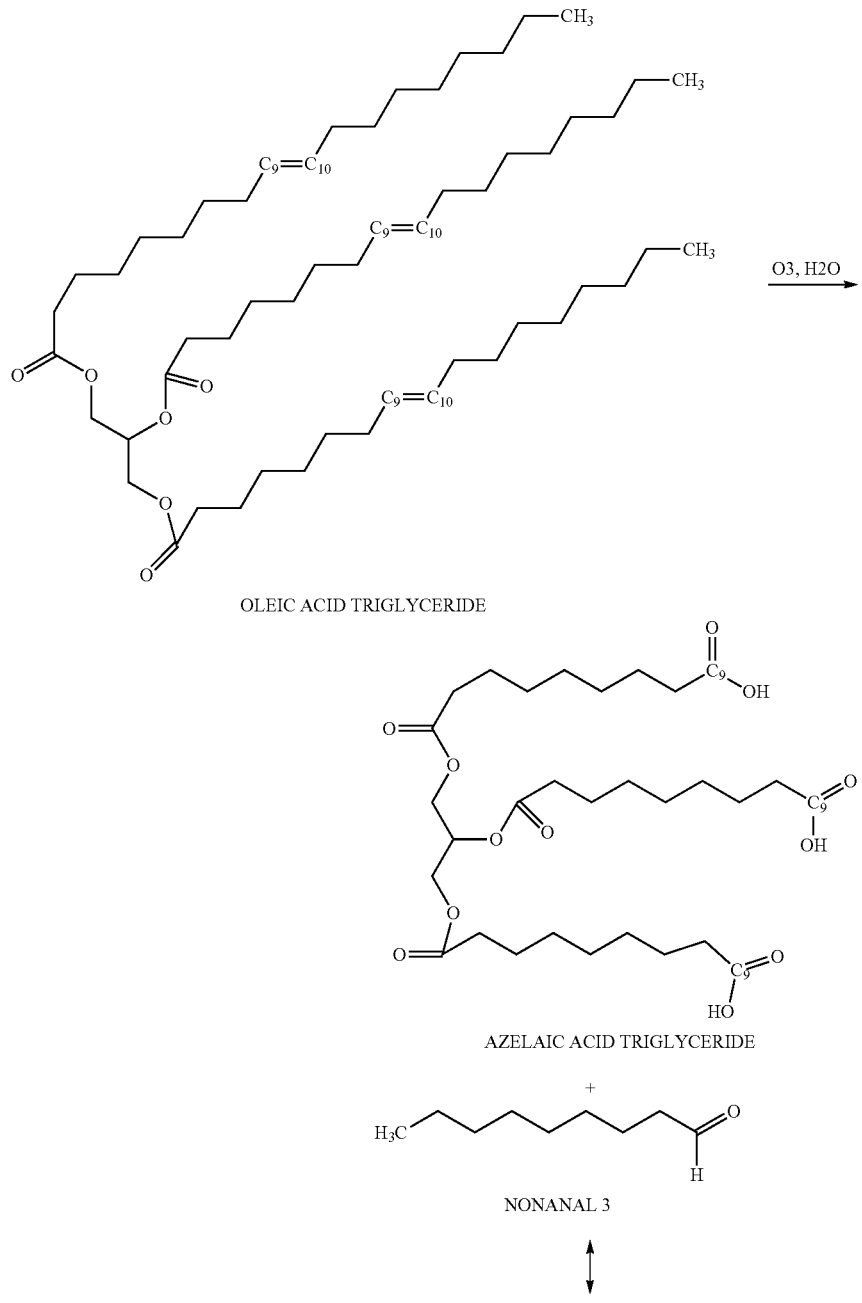

-continued
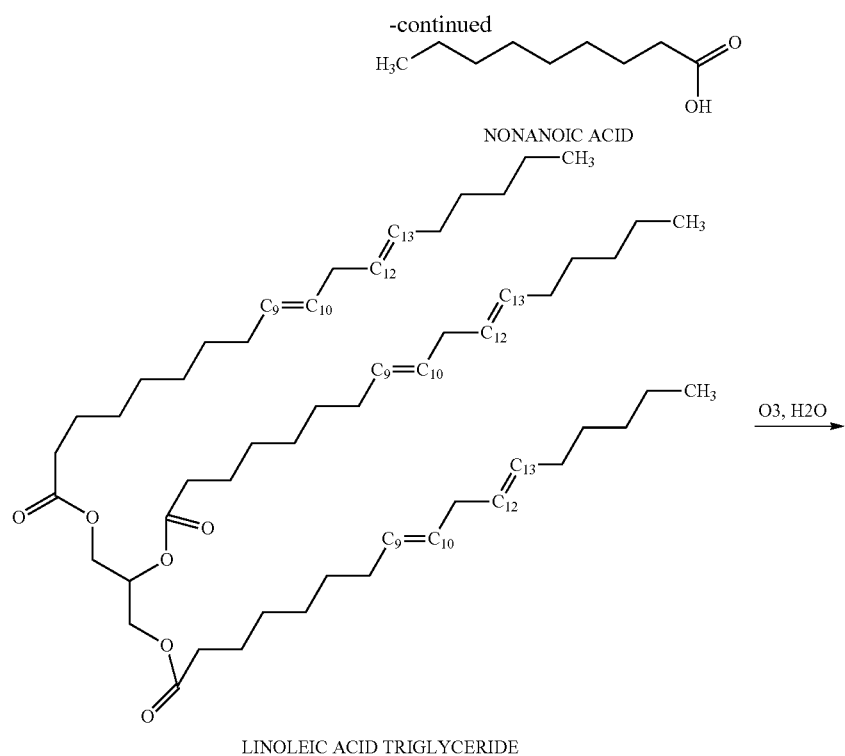
NONANOIC ACID
LINOLEIC ACID TRIGLYCERIDE
$O_3, H_2O$ →
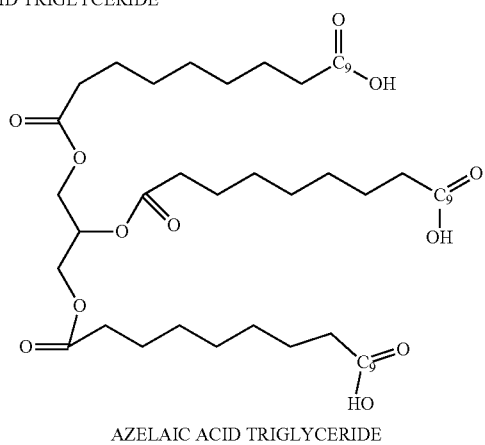
AZELAIC ACID TRIGLYCERIDE
+
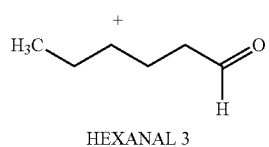
HEXANAL 3
↕
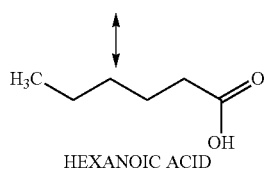
HEXANOIC ACID
+
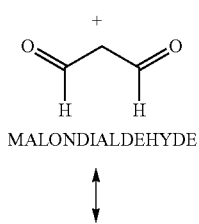
MALONDIALDEHYDE
↕

-continued

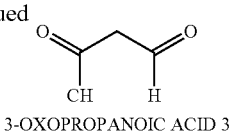

3-OXOPROPANOIC ACID 3

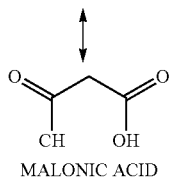

MALONIC ACID

Heat Treatment of Ozonated Vegetable Oil Composition

After ozonation, an ozonated vegetable oil composition can undergo a heat treatment so that one or more ozonide reaction products from ozonation can be decomposed into one or more components that, while not being bound by theory, are believed to be effective as active components of an antimicrobial composition and/or a virucidal disinfectant composition. Non-limiting examples of such active components in include one or more aldehydes, one or more carboxylic acids, and combinations thereof.

In some embodiments, such active components are soluble in water. Non-limiting examples of such carboxylic acids include one or more monocarboxylic acids, one or more dicarboxylic acids, and combinations thereof. Further, non-limiting examples of such carboxylic acids include one or more C1 to C4 carboxylic acids, or even one or more C1 to C3 carboxylic acids. Non-limiting examples of C1 to C4 acids include formic acid (C1 acid), acetic acid (C2 acid), malonic acid (C3 acid), lactic acid (C3 acid), succinic acid (C4 acid), and combinations thereof. One or more carboxylic acids can be present in the aqueous phase in an amount that provides desirable antimicrobial and/or virucidal disinfectant properties. In some embodiments, one or more C1 to C4 carboxylic acids can be present in an amount up to 20 percent by total weight of the aqueous fraction that is present in heat-treated, ozonated vegetable oil composition and that can be separated therefrom as described herein. For example, one or more C1 to C4 carboxylic acids can each be present in an amount from 0.1 to 15 percent, from 0.5 to 15 percent, from 1 to 15 percent, from 2 to 15 percent, from 3 to 15 percent, from 0.5 to 10 percent, or even from 1 to 5 percent by total weight of the aqueous fraction that is present in heat-treated, ozonated vegetable oil composition.

An ozonated vegetable oil composition can undergo a heat treatment at a variety of temperatures. Ozonides tend to decompose at a faster rate as the temperature increases. In some embodiments, an ozonated vegetable oil composition can be exposed to a temperature of 50° C. or greater (e.g., from 50° C. to 200° C., from 50° C. to 120° C., from 50° C. to 100° C., from 50° C. to 95° C., from 50° C. to 60° C., from 90° C. to 130° C., from 60° C. to 100° C., from 80° C. to 100° C., or even from 75° C. to 95° C.).

An ozonated vegetable oil composition can undergo a heat treatment for a variety of time periods, which can depend on the temperature of the heat treatment. In some embodiments, an ozonated vegetable oil composition can undergo a heat treatment for a time period of at least one minute (e.g., from one minute to 48 hours, from 12 hours to 24 hours, or even from 30 minutes to 4 hours). An ozonated vegetable oil composition can undergo a heat treatment at a variety of pressures, which can depend on the temperature of the heat treatment. In some embodiments, an ozonated vegetable oil composition can undergo a heat treatment at a temperature and pressure that is below the boiling point of the ozonated vegetable oil composition. For example, an ozonated vegetable oil composition can be exposed to higher temperatures as the pressure increases. In some embodiments, an ozonated vegetable oil composition can undergo a heat treatment at atmospheric pressure or at a pressure greater than atmospheric pressure (e.g., greater than 1 atmosphere).

An ozonated vegetable oil composition can undergo a heat treatment using a variety of heating techniques such as heating the ozonated vegetable oil composition while it is in a vessel (e.g., with or without stirring), flowing the ozonated vegetable oil composition through a heat exchanger such a jacketed vessel, a plate and frame heat exchanger, a shell and tube heat exchanger, combinations of these and the like.

During the heat treatment, an ozonated vegetable oil composition may or may not have an aqueous phase (e.g., a weight ratio of vegetable oil component to water as described above) due to added water. Including added water in the ozonated vegetable oil composition during heat treatment is advantageous because the water present in the aqueous phase can help partition water-soluble components such as aldehydes and/or carboxylic acids that may be formed during heat treatment into the aqueous phase, which can be recovered to form an antimicrobial composition and/or a virucidal disinfectant composition, as discussed below.

Alternatively, a vegetable oil composition can have no added water present during a heat treatment and, thus, include a relatively low amount of moisture content during the heat treatment (e.g., from 0.1 to 1 percent by weight of the total vegetable oil composition).

Optionally, after heat treatment, an ozonated vegetable oil composition (with or without an aqueous phase) can be subjected to an aqueous washing process to recover water-soluble components including one or more components that may be active antimicrobial compounds. Washing an ozonated vegetable oil composition after heat treatment may be especially desirable if an ozonated vegetable oil composition has little to no moisture content to help separate such water-soluble components from an oil phase of the ozonated vegetable oil composition. An organic solvent, if any, can impact the reaction products from ozonation and/or after subsequent heat treatment. In some embodiments, ozonolysis and/or subsequent heat treatment does not occur in the presence of an exogenous amount of organic solvent, including an organic solvent that is a product of ozonolysis and the heat treatment decomposition reaction, respectively. Advantageously, methods according to the present disclosure can be performed without adding any additional materials if desired. In some embodiments, an aqueous composition such as water and/or an aqueous process stream is the only added material as described herein.

It is noted that ozone tends to decompose faster as the temperature increases. Thus, a heat treatment according to the present disclosure can also increase the rate at which ozone is removed from an ozonated, vegetable oil composition. Ozone gas concentration can also be removed from an ozonated vegetable oil composition prior to and/or during subsequent heat treatment using one or more other techniques such as gas (e.g., air) stripping the ozonated vegetable oil composition. In some embodiments, to obtain desirable active components for an antimicrobial composition and/or a virucidal disinfectant composition, no ozone gas is introduced into the ozonated vegetable oil composition prior to and/or during subsequent heat treatment. In some embodiments, it is desirable to decrease the concentration of ozone gas as much as possible prior to and/or during subsequent heat treatment so as to stop any further ozonolysis reactions. In some embodiments, the concentration of ozone gas in an ozonated vegetable oil composition during heat treatment is 10 percent or less, 5 percent or less, 1 percent or less, 0.5 percent or less, or even 0.1 percent or less by weight based on the total weight of the vegetable oil composition. The concentration of ozone can depend on the rate at which ozone was previously introduced into the vegetable oil composition during ozonolysis (e.g., sparging flow rate of ozone), and any subsequently processing that may have removed and/or decomposed the ozone.

The time period ("lag time") between exposing a vegetable oil composition to ozone gas (e.g., introducing ozone gas into the vegetable oil composition) and downstream processing such as subsequent heat treatment of an ozonated vegetable oil composition can be selected as desired. In some embodiments, the time period can be selected to reduce the concentration of ozone gas as soon as possible so as to stop any further ozonolysis reactions. As discussed above, increasing the temperature of the ozonated vegetable oil composition can cause any residual ozone gas to decompose. In some embodiments, the time period between exposing a vegetable oil composition to ozone gas (e.g., introducing ozone gas into the vegetable oil composition) and downstream processing such as subsequent heat treatment of an ozonated vegetable oil composition can be less than 2 hours, less than 1 hour, less than 30 minutes, or even less than 10 minutes.

Separating Two or More Phases to Recover One or More Antimicrobial Compositions and/or a One or More Virucidal Disinfectant Compositions After heat-treating the ozonated vegetable oil composition as described above to decompose ozonides, at least a portion of an aqueous phase can be separated from the ozonated vegetable oil composition. In some embodiments, the portion of the aqueous phase separated from the ozonated vegetable oil composition can be used as an antimicrobial composition and/or a virucidal disinfectant composition. In some embodiments, the remaining portion (e.g., the oil phase) of the ozonated vegetable oil composition can be used as an antimicrobial composition and/or a virucidal disinfectant composition.

A wide variety of techniques can be used to separate at least a portion of an aqueous phase can be separated from the ozonated vegetable oil composition. For example, at least a portion of an aqueous phase can be separated from the ozonated vegetable oil composition based on density differences (e.g., using one or more of a settling tank, a centrifuge, and the like). In some embodiments, the aqueous phase and oil phase can be separated from the ozonated vegetable oil composition to form an antimicrobial and/or virucidal composition without altering the composition of the ozonated vegetable oil composition, the separated aqueous phase, and/or the separated oil phase. If desired, one or more additional components could be added to an otherwise unaltered ozonated vegetable oil composition, separated aqueous phase, and/or separated oil phase.

Antimicrobial Compositions

As mentioned above, the oil phase (oil carrier), aqueous phase (aqueous carrier), or tailored mixture thereof that is recovered from a heat-treated ozonated vegetable oil composition can be used as an antimicrobial composition. As used herein, an "antimicrobial" composition refers to a composition that includes one or more compounds that can kill one or more microorganisms and/or stops the growth of one or more microorganisms. Table 1 below illustrates representative compounds and amounts that may be present in a heat-treated, ozonated vegetable oil composition (or an oil phase separated therefrom or an aqueous phase separated therefrom) made according to the present disclosure and that may be used an antimicrobial composition. Ozonating heating may be performed to provide a tailored antimicrobial composition that includes one or more of the compounds listed in Tables 1, 2 or 3 below.

TABLE 1

Average Characterization of Oil and Aqueous Phases of an Ozonated/Heat-treated Vegetable Oil Composition

| Compound | MIN | MAX | AVG | STDEV |
| --- | --- | --- | --- | --- |
| Hexanal (%) | 0.21 | 4.20 | 1.69 | 0.0122 |
| Hexanal dimethyl acetal (%) | 0.39 | 3.68 | 1.71 | 0.0104 |
| Methyl hexanoate (%) | 0.61 | 9.20 | 3.87 | 0.0266 |
| Nonanal (%) | 0.15 | 5.32 | 1.94 | 0.0177 |
| Methyl 3,3-dimethoxypropionate (%) | 0.19 | 3.83 | 1.67 | 0.0132 |
| Nonanal dimethyl acetal (%) | 0.48 | 4.93 | 2.41 | 0.0144 |
| Methyl nonanoate (%) | 0.41 | 11.83 | 3.35 | 0.0276 |
| Dimethyl malonate (%) | 0.04 | 2.15 | 0.77 | 0.0071 |
| Dimethyl azelate (%) | 1.36 | 16.24 | 8.26 | 0.0477 |
| Methyl palmitate (%) | 7.18 | 35.23 | 14.32 | 0.1066 |
| Methyl palmitoleate (%) | 0.22 | 1.33 | 0.88 | 0.0060 |
| Methyl stearate (%) | 2.87 | 6.45 | 4.06 | 0.0207 |
| Methyl oleate (%) | 0.36 | 14.31 | 5.56 | 0.0458 |
| Methyl linoleate (%) | 0.09 | 17.57 | 5.15 | 0.0594 |
| Methyl hydrogen azelate (%) | 2.87 | 2.88 | 2.87 | 0.00003 |

Methods of Using Antimicrobial Compositions

Embodiments of the present disclosure include methods of sanitizing a surface that include contacting the surface with an antimicrobial composition according to the present disclosure. A wide variety of surfaces can be treated with an antimicrobial composition according to the present disclosure. Non-limiting examples of surfaces include one or more equipment surfaces in a food processing facility (e.g., tables, conveyors, etc.), equipment surfaces in a biorefinery (e.g., tanks, vessels, valves, pumps and/or piping) such as fermentation equipment surfaces (e.g., to control microbial contamination). In some embodiments, contacting equipment surfaces with the antimicrobial composition include flushing equipment (e.g., tanks, vessels, valves, pumps and/or piping) with the antimicrobial composition. Flushing equipment can be referred to as "clean in place" (CIP). Advantageously, antimicrobial compositions derived from vegetable oil compositions according to the present disclosure can avoid, if desired, having to use cleaners such as hot caustic solutions. Some caustic solutions include sodium, which can cause problems in a biorefinery if residual amounts remain after cleaning. Accordingly, antimicrobial compositions according to the present disclosure can be non-sodium based since they are derived from vegetable oil compositions such as, e.g., distiller's corn oil. In some embodiments, the volume of antimicrobial composition that is used for CIP can be relatively small as compared to the overall water balance and the antimicrobial acids would be sufficiently diluted after CIP such that they would not cause problems downstream such as in DDGS or an anaerobic digester.

Embodiments of the present disclosure also include methods of controlling microbial contamination during fermentation by adding one or more doses of an antimicrobial composition according to the present disclosure to a fermentation broth (e.g., to control undesirable microbial contamination such as lactic acid bacteria without inhibiting desirable microorganisms (e.g., yeast) to an undue degree). In some embodiments, an amount of an antimicrobial composition according to the present disclosure is added to the fermentation broth that balances the efficacy for the target microorganism while at the same time does not impact non-target (e.g., desired) microorganisms (e.g., yeast) to an undue degree. In some embodiments, an antimicrobial composition is added in an amount from 1 to 3 percent by weight based on the total weight of the fermentation broth.

Embodiments of the present disclosure include methods of preserving a perishable food or feed by contacting the perishable food or feed (e.g., wet cake) with an antimicrobial composition according to the present disclosure.

Embodiments of the present disclosure also include methods of promoting growth in an animal (cattle, pigs, poultry, etc.). Such methods can include feeding the animal a ration that includes at least an aqueous phase derived from exposing a vegetable oil composition to ozone gas to form an ozonated vegetable oil composition (an ozonated vegetable oil composition can include the aqueous phase and an oil phase). In some embodiments, the ration includes the ozonated vegetable oil composition (e.g., ozonated distiller's grain oil) including both the aqueous phase and oil phase. In some embodiments, the aqueous phase can be separated from the ozonated vegetable oil composition prior to being included in a ration.

Embodiments of the present disclosure also include methods of forming an animal feed supplement to promote gut health in an animal (e.g., monogastric animals). In some embodiments, the method includes exposing a vegetable oil composition to ozone gas to form an ozonated vegetable oil composition, as described herein, which can include an aqueous phase and an oil phase, or only an oil phase (e.g., water has not been added to the vegetable oil composition before, during or after ozonation).

In some embodiments, whether or not the ozonated vegetable oil composition includes an aqueous phase, at least a portion of the oil phase can be separated from/recovered from the ozonated vegetable oil composition and used as the animal feed supplement as-is, or combined with one or more additional materials to form an animal feed supplement.

The free fatty acid content of a vegetable oil composition can be modified by methods of the present disclosure. In some embodiments, the free fatty acid content of a given free fatty acid can be increased or decreased using method of the present disclosure. One or more conditions such as ozonating time, ratio of volumetric flow of ozone gas to volume of vegetable oil composition; time of ozonation; whether ozonating and/or heat-treating is performed in the presence of water; time of heat treatment; temperature of heat treatment and whether an ozonated vegetable oil is washed with water can be selected to tailor the free fatty acid profile of the oil phase or aqueous phase recovered from a heat-treated, ozonated vegetable oil composition.

In some embodiments, the oil phase includes a free fatty acid chosen from Caproic Acid, Caprylic Acid, Capric Acid, Lauric Acid, Myristic Acid, Palmitic Acid, Palmitoleic Acid, Margaric Acid, Stearic Acid, Oleic Acid, Vaccenic Acid, Linoleic Acid, alpha-Linolenic Acid, and mixtures thereof.

As mentioned, one or more free fatty acids can be present in an oil phase recovered from a heat-treated, ozonated vegetable oil composition in an amount greater than prior to ozonation. In some embodiments, an oil phase recovered from a heat-treated, ozonated vegetable oil composition can have one or more free fatty acids chosen from Caproic Acid, Caprylic Acid, Capric Acid, Lauric Acid, Myristic Acid, Palmitoleic Acid, Oleic Acid, Vaccenic Acid, alpha-Linolenic Acid, where each chosen fatty acid is in an amount from 0.05 to 200, from 0.05 to 100, from 0.05 to 50, from 0.05 to 25, or even from 0.05 to 10 milligrams of fatty acid per gram of oil phase recovered from the heat-treated, ozonated vegetable oil.

As mentioned, one or more free fatty acids can be present in an oil phase recovered from a heat-treated, ozonated vegetable oil composition in an amount less than prior to ozonation. In some embodiments, an oil phase recovered from a heat-treated, ozonated vegetable oil composition can have one or more free fatty acids chosen from Palmitic Acid, Stearic Acid, Oleic Acid, Linoleic Acid, where each chosen free fatty acid is in an amount from 0.05 to 20, from 0.05 to 15, from 0.05 to 10, from 0.05 to 5, or even from 0.05 to 2.5 milligrams of fatty acid per gram of oil phase recovered from the heat-treated, ozonated vegetable oil.

Free fatty acid content can be determined by test method AOCS Ca 5a-40.

Virucidal Disinfectant Compositions and Uses

Embodiments of the present disclosure also include methods of making one or more virucidal disinfectant compositions. As used herein, a "virucidal disinfectant composition" refers to a composition that can deactivate or destroy at least one virus (enveloped and/or non-enveloped viruses) after contacting the virus.

Methods of making a virucidal disinfectant compositions can be made in a similar or the same manner as making antimicrobial compositions as described herein, but may be tailored if desired to obtain a profile of active compounds that have desired virucidal efficacy with respect to a given virus.

In some embodiments, a method of making a virucidal disinfectant composition includes exposing a vegetable oil composition to ozone gas to form an ozonated vegetable oil composition that includes an aqueous phase and an oil phase, followed by separating at least a portion of the aqueous phase from the ozonated vegetable oil composition. The aqueous phase from the ozonated vegetable oil composition can be a virucidal disinfectant composition and/or the oil phase from the ozonated vegetable oil composition can be a virucidal disinfectant composition. In some embodiments, a virucidal disinfection composition can include one or more of compounds listed herein in Tables 1, 2 and/or 3.

A virucidal disinfectant composition made according to the present disclosure can be applied to a wide variety of surfaces to disinfect such surfaces against virus activity. The surface selected for treatment can depend on whether the oil or aqueous phase is used directly or if the oil or aqueous phase is combined with one or more additional ingredients to make the virucidal disinfectant composition have more virucidal activity and/or to make the virucidal disinfectant composition more compatible with a surface to be treated.

Non-limiting examples of such surfaces include metal, wood and plastic surfaces, especially such surfaces that come into contact with skin surfaces such as tabletops, door handles, steering wheels, and the like. Also, such surfaces can include hand surfaces (e.g., when used as a hand sanitizer).

A virucidal disinfectant composition made according to the present disclosure can be used directly after being recovered from an ozonated vegetable oil composition as described herein, or it can be combined with one or more added (exogenous) ingredients to increase its virucidal activity and/or to make it more compatible with the surface it is intended to treat. Non-limiting examples of such ingredients include one or more alcohols (e.g., ethanol, isopropyl alcohol, and the like), aloe vera gel, one or more essential oils, one or more organic acids (polycarboxlyic acids such as citric acid), urea, one or more quaternary ammonium compounds, hydrogen peroxide, one or more inorganic acids (e.g., hydrochloric acid (HCl), nitric acid (HNO3), boric acid (H3BO3), sulfuric acid (of H2SO4), carbonic acid (H2CO3), phosphoric acid (of H3PO4), etc.).

Example 1

Corn oil (150-300 grams) was first ozonated by sparging a 15-25 g/hr ozone stream into the corn oil for 2-4 hours. An ice bath (~4° C.) was used to prevent a runaway reaction and keep the temperature below ~40° C. The control was corn oil that did not undergo ozonation or subsequent heat treatment. The "ozonated oil" was corn oil that was ozonated as-is. The "ozonated oil-water mixture" was corn oil that was ozonated at a 1:2 mass ratio with added water. Water helps take up excess heat generated from the ozonolysis reaction and also helps drive intermediates and aldehydes to acids. Ozonation formed unstable ozonide compounds, which were stabilized by a subsequent heat treatment. The heat treatment involved heating each ozonated sample ("ozonated oil" and "ozonated oil-water mixture") to 100-120° C. for 1-2 hours, which decomposed the ozonides to aldehydes and carboxylic acids. After the heat treatment of the "ozonated oil=H$_2$O" same, the oil-water mixture was separated into an oil phase and an aqueous phase. The results of the oil phases are shown in Table 2 and the result of the aqueous phase is shown in Table 3 below. As shown in Table 2 below, for the oil phase made from the water-oil mixture, the saturated acids/aldehydes ratio was more than double that of the corn oil as-is ozonated sample.

TABLE 2

Composition data is shown for corn oil, ozonated corn oil (as-is), and ozonated corn oil-water mix. *There was some contamination in the GC column which is why the mass balance is over 100%.

| Sample | Control | Ozonated Oil | Oil phase from ozonated Oil-water mixture |
|---|---|---|---|
| Identified Components (%) | 123.4 | 100.5 | 113.6 |
| Unsaturated Fat (%) | 73.5 | 8.8 | 41.3 |
| Saturated Fat (%) | 26.5 | 91.2 | 58.7 |
| Sat. Monoacids | 3.7 | 20.3 | 12.0 |
| Sat. Diacids | 8.8 | 30.5 | 19.6 |
| Sat. Monoaldehydes | 0.0 | 16.8 | 4.0 |
| Sat. Acids/Aldehyde ratio | 0.0 | 3.0 | 7.9 |
| Sat. Aldehyde-Acid | 0.0 | 5.3 | 2.1 |
| Hexanal | 0.0 | 7.9 | 1.9 |
| Hexanoic Acid | 0.0 | 9.7 | 4.4 |
| Nonanal | 0.0 | 8.9 | 2.1 |

TABLE 2-continued

Composition data is shown for corn oil, ozonated corn oil (as-is), and ozonated corn oil-water mix. *There was some contamination in the GC column which is why the mass balance is over 100%.

| Sample | Control | Ozonated Oil | Oil phase from ozonated Oil-water mixture |
|---|---|---|---|
| 3-Oxopropanoic Acid | 0.0 | 5.3 | 2.1 |
| Nonanoic Acid | 1.6 | 7.7 | 4.6 |
| Malonic Acid | 1.8 | 4.0 | 2.8 |
| Azelaic Acid | 7.0 | 26.6 | 16.8 |
| Palmitic Acid | 14.0 | 18.2 | 17.9 |
| Palmoleic Acid | 2.1 | 2.9 | 3.0 |
| Oleic Acid | 25.0 | 4.6 | 17.0 |
| Linoleic Acid | 48.5 | 4.2 | 24.3 |

TABLE 3

Composition data is shown for the water fraction of the ozonated corn oil/water mixture.

| Component | Concentration (mg/L) |
|---|---|
| Formic Acid | 8995 |
| Acetic Acid | 6102 |
| Malonic Acid | 1050 |
| Lactic Acid | 109 |
| Succinic Acid | 90 |

The C3 diacid, malonic acid, is toxic for antimicrobial purposes, but because of its molecular geometry, it can rapidly break down by exposure to ozone. But, as shown in Tables 2 and 3 above, malonic acid is present after ozonation. While not being bound by theory, this may be due chemical reactions not being complete while the corn oil is exposed to ozone, which can therefore result in at least a portion of the malonic acid that is produced not exposed to ozone. Because at least a portion of the malonic acid is not exposed to ozone it does not react with ozone and breakdown. Further, exposing ozonated grain oil to a heating step can breakdown at least a portion of any remaining ozone and ozonated products into their stable forms thereby reducing the likelihood of malonic acid being exposed to ozone. Thus, reaction between malonic acid (and any other desirable antimicrobial compounds) can essentially be halted, thereby allowing for the stabilization of malonic acid. Thus, controlling exposure to ozone by controlling the introduction of new ozone into a grain oil and/or the timing of a heating step can tailor the compositional profile of an antimicrobial composition according to the present disclosure.

The ozonated oil samples (ozonated corn oil (as-is), and oil phase separated from the ozonated corn oil-water mix) were evaluated for antimicrobial activity by performing growth curves with *Escherichia coli* (representing gram negative bacteria) and probiotic (representing gram positive bacteria). Treatment levels for *E. coli* were from 0.02 wt % to 10 wt %. Since no effect was observed at 0.02 wt % and no growth was observed above 2 wt %, the treatment levels were changed for more resolution with the probiotic growth curve. The treatments for the probiotic, was between 0.2% to 5 wt %. The data showed that probiotic growth was inhibited for treatments with both ozonated corn oil (as-is) and oil phase separated from the ozonated corn oil-water mix at doses above 1 wt %, with no growth observed above 2 wt %.

The aqueous phase separated from ozonated corn oil-water mix after the ozonation process was dosed at varying levels into a fermentation mash. The ethanol yield at the end of fermentation was measured as well as the lactic acid concentration throughout fermentation. Data showed that the most beneficial doses were at 1% and 3% because the production of lactic acid by lactic acid bacteria was controlled to within acceptable levels while at the same not impacting the production of ethanol due to yeast activity to an undue degree.

Example 2

Ozonated Oil as Wet Cake Preservative

Five samples each weighing approximately 10 lbs were tested for mold growth after 7 days at ambient conditions exposed to air. Below are the visual results, showing the day 0 and day 7 appearance for the following tested conditions; an untreated control, a 0.25% propionic acid treatment, 0.25% ozonated oil treatment, and 0.50% ozonated oil treatment. The oil used for treatment was as-is and did not include added water. The oil was treated by adding water at a 1:2 ratio (oil:water). Ozone treatment was 6 lpm, at 4-5.5% ozone concentration over 5 hours using ice to maintain the temperature between 17 and 45 C over the course of the treatment. After ozone treatment, the sample was heat treated at 91-93 C for 1.5 hrs.

Additionally, but not shown is another control kept at 4° C. over the duration of the experiment. Propionic acid treatments were applied as a 50/50 solution with water and sprayed over the wet cake and mixed by hand.

Figures 2A, 2B:
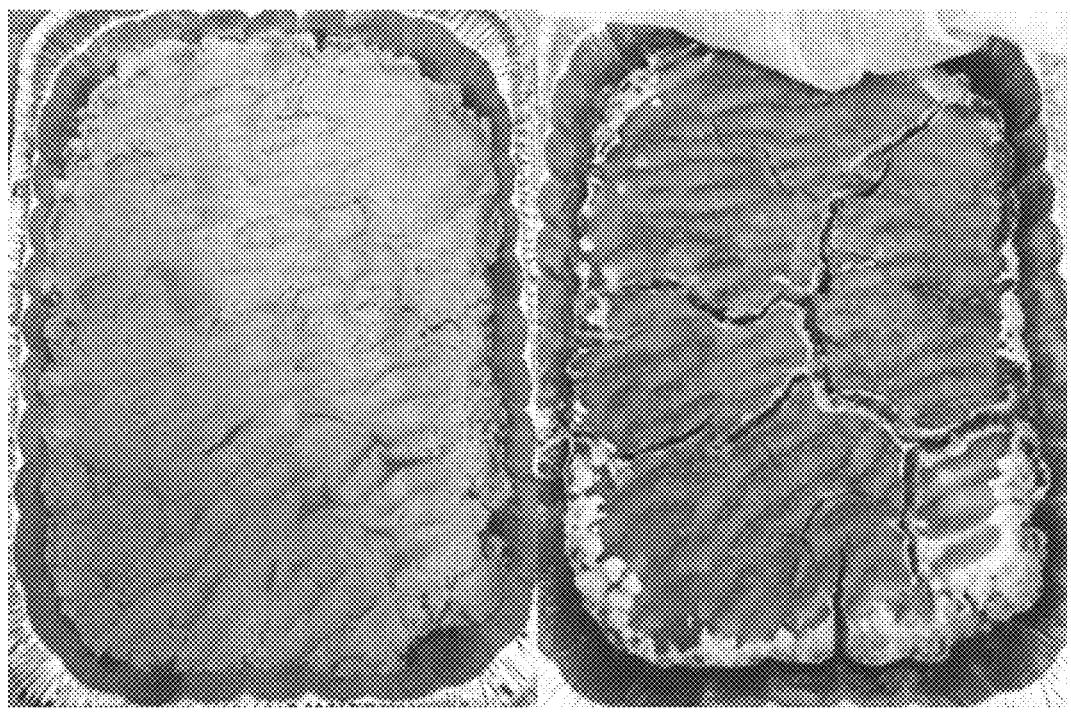
Figures 3A, 3B:
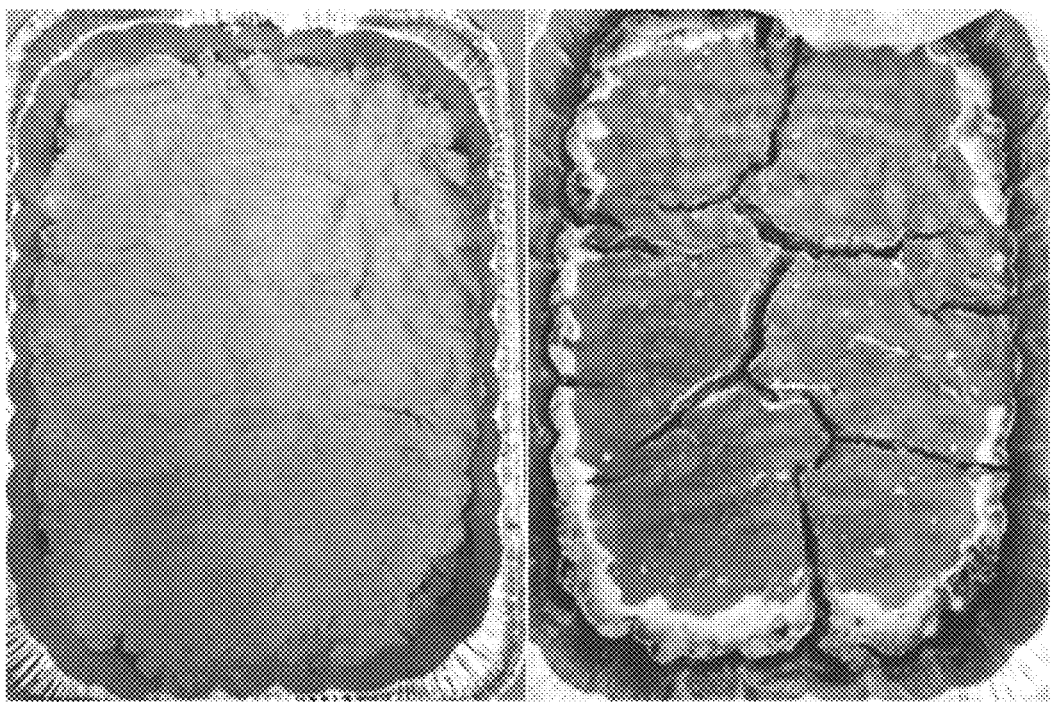
Figures 4A, 4B:
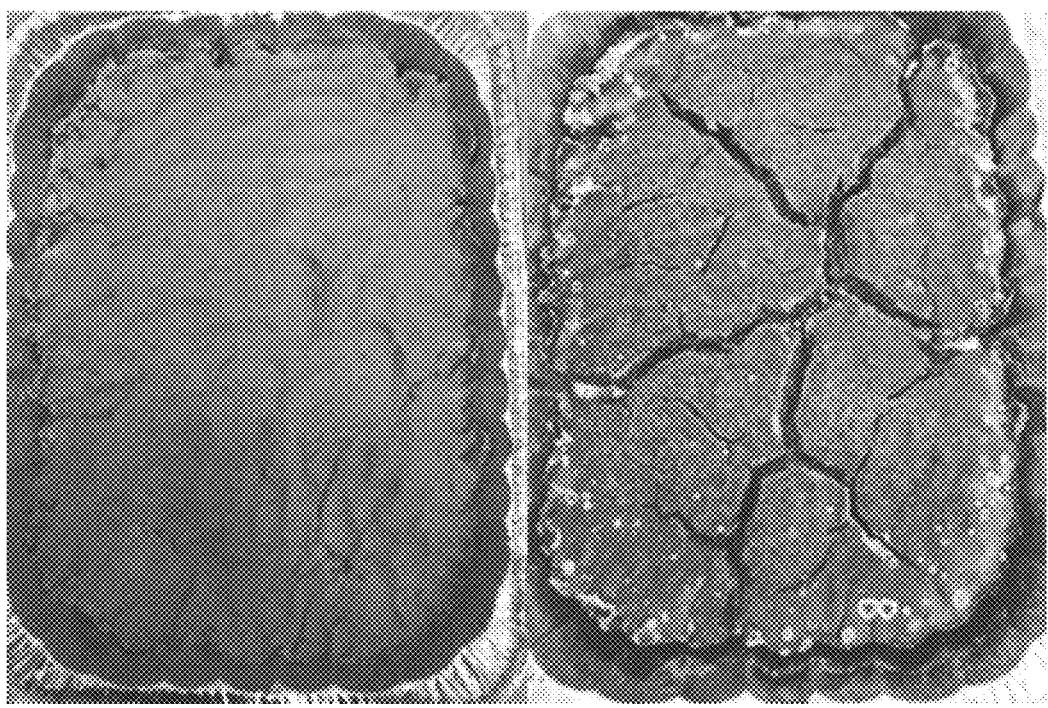

The ozonated oil treatments were applied as a spray diluted 50/50 with clarified corn oil, not water. Oil treatments were also hand kneaded into the wet cake due to the oil spray not having as much coverage as the aqueous propionic acid solution. FIGS. 1A-4B show photographs of each wet cake sample at 0 days and 7 days at ambient conditions. FIG. 1A shows a control wet cake sample at 0 days and FIG. 1B shows the control wet cake after 7 days at ambient conditions. FIG. 2A shows a wet cake sample with a 0.25% dose of propionic acid at 0 days and FIG. 2B shows the wet cake sample with a 0.25% dose of propionic acid after 7 days at ambient conditions. FIG. 3A shows a wet cake sample with a 0.25% dose of ozonated oil at 0 days and FIG. 3B shows the wet cake sample with a 0.25% dose of ozonated oil after 7 days at ambient conditions. FIG. 4A shows a wet cake sample with a 0.50% dose of ozonated oil at 0 days and FIG. 4B shows the wet cake sample with a 0.50% dose of ozonated oil after 7 days at ambient conditions.

The dry matter loss, protein loss, and net energy gain (NEG) lost were determined for the control and treated wet cake samples. An increase in dry matter loss is considered to reflect an increase in microbial activity on dry matter. This data showed that in comparison to treatment with propionic acid, which is relatively common treatment to extend the life of wet cake, the ozonated oil performed better, with less loss of material over the same span as the propionic acid. This suggests that the mixture of acids produced in the ozonation is a more effective bottom line product than propionic acid alone. The ozonated oil could be used at a facility to preserve wet cake for a longer period of time, or could be used as a potential product to consumers to prolong the use of the wet cake on the farm.

Example 3

The data in Table 4 below shows free fatty acid profile for three different samples. The Corn Oil Control was not exposed to ozone.

The Prototype 1 sample was a corn oil phase that was formed by exposing the corn oil, without added water, to ozone to form an ozonated corn oil, followed by heating the ozonated oil to decompose residual ozonides and form Prototype 1. The conditions used to form Prototype 1 were as follows:

Ozone at 4.7% average concentration;
Flow rate of Ozone=3.75 lpm;
240 min exposure time to ozone; and
70 min heating cycle at 90-120 C after ozonation to decompose residual ozonides.

The Prototype 2 sample was a corn oil phase that was formed by adding water to corn oil, exposing the corn oil/water mixture to ozone to form an ozonated corn oil, followed by heating the ozonated oil to decompose residual ozonides and then separating the aqueous phase, thereby leaving the remaining ozonated corn oil phase (i.e., Prototype 2). The conditions used to form Prototype 2 were as follows:

Ozone at 4.8% average concentration;
Flow rate of Ozone 2.25 lpm;
240 min exposure time to ozone; and
60 min heating cycle at 94 C after ozonation to decompose residual ozonides.

Either the Prototype 1 or the Prototype 2 could be useful as an animal feed supplement to promote gut health in an animal (e.g., monogastric animals), for example, due to the presence and amount of one or more C6 to C16 free fatty acids.

As can be seen in Table 4, the Prototype 2 oil had higher levels of Palmitoleic Acid, Margaric Acid, Vaccenic Acid, and alpha-Linolenic Acid as compared to Prototype I and the control. While not being bound by theory, this may be due to the presence of water favoring the formation of these compounds and/or one or more compounds in the "others" category in Table 4. Also, while not being bound by theory, one or more free fatty acids in Prototype 2 that are present in an amount less as compared to Prototype 1 may be due to at least a portion of said one or more free fatty acids being partitioned in the aqueous phase that was separated in forming Prototype 2.

Accordingly, ozonating followed by heat treating a water/oil mixture according to the present disclosure and then separating an oil phase can permit a fatty acid profile of the oil phase to be tailored as desired for purposes such as forming an animal feed supplement.

TABLE 4

| | Corn Oil Control (mg FA/g) | Corn Oil Prototype 1 (mg FA/g) | Corn Oil Prototype 2 (mg FA/g) |
|---|---|---|---|
| C6 Caproic | 0 | 51 | 16.8 |
| C8 Caprylic | 0 | 5.3 | 1.4 |
| C10 Capric | 0 | 0.4 | 0.2 |
| C12 Lauric | 0 | 0.2 | 0.2 |
| C14 Myristic | 0.5 | 0.7 | 0.6 |
| C16 Palmitic | 119.1 | 0.2 | 0.3 |
| C16:ln7 Palmitoleic | 1.7 | 108.6 | 117.4 |
| C17 Margaric | 0.6 | 0.4 | 1.3 |
| C18 Stearic | 17.3 | 0.7 | 0.7 |
| C18:ln9 Oleic | 239 | 16 | 17.5 |
| C18:ln7 Vaccenic | 4.3 | 19 | 125.8 |
| C18:2 Linoleic | 476 | 4.3 | 2.6 |
| C18:3n3 alpha-Linolenic | 11.1 | 14.7 | 180 |
| C20 Arachidic | 3.7 | 0.2 | 3.4 |
| C20:1 Eicosenoic | 2.9 | 3.6 | 3.8 |
| C20:2n6 Eicosadienoic | 0.3 | 10.2 | 7.5 |

TABLE 4-continued

| | Corn Oil Control (mg FA/g) | Corn Oil Prototype 1 (mg FA/g) | Corn Oil Prototype 2 (mg FA/g) |
|---|---|---|---|
| C22 Behenic | 1.6 | 1.5 | 1.6 |
| C24 Lignoceric | 2 | 1.8 | 2 |
| Others: | 2.4 | 189.1 | 102.2 |
| TFA: | 882.5 | 427.9 | 585.3 |
| Total Saturates | 144.8 | 190 | 162.5 |
| Total MonoUnsaturated | 247.9 | 33.9 | 137.2 |
| Total PolyUnsaturated | 487.4 | 14.9 | 183.4 |
| Total Omega 3 | 11.1 | 0.2 | 3.4 |
| Total Omega 6 | 476 | 14.7 | 180 |
| Total Omega 9 | 241.9 | 29.2 | 133.3 |

Prototype 1: Ozonated Oil Alone
Prototype 2: Ozonated Oil:Water Mixture, followed by separating oil phase from aqueous phase leaving oil phase as Prototype 2.

Following are exemplary, additional embodiments of the present disclosure:

1) An antimicrobial composition and/or virucidal disinfectant composition comprising:
   a) an aqueous carrier;
   b) one or more of compounds listed in Tables 1, 2 and/or 3, wherein the one or more compounds are present in an amount due to ozonating, and optionally heating, a vegetable oil composition.

2) An antimicrobial composition and/or virucidal disinfectant composition comprising:
   a) an oil carrier;
   b) one or more of compounds listed in Tables 1, 2 and/or 3, wherein the one or more compounds are present in an amount due to ozonating, and optionally heating, a vegetable oil composition.

3) A method of sanitizing a surface comprising contacting the surface with an antimicrobial composition according to any preceding embodiment.

4) The method of embodiment 3, wherein the surface comprises an equipment surface in a food processing facility (e.g., tables, conveyors, etc.).

5) The method of embodiment 3, wherein the surface comprises equipment in a biorefinery (e.g., tanks, vessels, valves, pumps and/or piping) such as fermentation equipment (e.g., to control microbial contamination and includes flushing fermentation equipment with the antimicrobial composition).

6) The method of embodiment 3, wherein the surface is the surface of an animal carcass in a meat processing facility (beef, pork, poultry, etc.).

7) A method of controlling microbial contamination during fermentation, wherein the method comprises adding one or more doses of an antimicrobial composition according to embodiments 1 and/or 2 to a fermentation broth (e.g., to control undesirable microbial contamination such as lactic acid bacteria without inhibiting desirable microorganisms (e.g., yeast) to an undue degree).

8) The method of embodiment 7, wherein the antimicrobial composition is added in an amount from 1 to 3 percent by weight based on the total weight of the fermentation broth.

9) A method of preserving a perishable food or feed, wherein the method comprises contacting the perishable food or feed (e.g., wet cake) with an antimicrobial composition according to embodiments 1 and/or 2.

10) A method of promoting growth in an animal (cattle, pigs, poultry, etc.), wherein the method comprises feeding the animal a ration comprising an aqueous phase derived from exposing a vegetable oil composition to ozone gas to form an ozonated vegetable oil composition, wherein the ozonated vegetable oil composition comprises the aqueous phase and an oil phase.

11) The method of embodiment 10, wherein the ration includes the ozonated vegetable oil composition (e.g., ozonated distiller's grain oil).

12) The method of embodiment 10, wherein the aqueous phase has been separated from the ozonated vegetable oil composition.

13) A method of forming an animal feed supplement to promote gut health in an animal (e.g., monogastric animals)), wherein the method comprises: a) exposing a vegetable oil composition to ozone gas to form an ozonated vegetable oil composition, wherein the ozonated vegetable oil composition comprises an aqueous phase and an oil phase, and
   b) separating at least a portion of the oil phase from the ozonated vegetable oil composition, wherein the at least a portion of the oil phase from the ozonated vegetable oil composition is the animal feed supplement.

14) The method of embodiment 30, wherein the oil phase comprises one or more free fatty acids chosen from Caproic Acid, Caprylic Acid, Capric Acid, Lauric Acid, Myristic Acid, Palmitic Acid, Palmitoleic Acid, Margaric Acid, Stearic Acid, Oleic Acid, Vaccenic Acid, Linoleic Acid, alpha-Linolenic Acid, and mixtures thereof.

What is claimed is:

1. A method of making one or more antimicrobial compositions and/or one or more virucidal disinfectant compositions, wherein the method comprises:
   a) exposing a vegetable oil composition to ozone gas to cause ozonolysis of one or more unsaturated fatty acids present in the vegetable oil composition, thereby forming an ozonated vegetable oil composition, wherein the ozonated vegetable oil composition comprises one or more ozonide compounds;
   b) exposing the ozonated vegetable oil composition to a temperature greater than 60° C. while in contact with water to decompose one or more ozonide compounds and form a heat-treated, ozonated vegetable oil composition comprising a carboxylic acid chosen from a C1 carboxylic acid, a C2 carboxylic acid, a C3 carboxylic acid, a C4 carboxylic acid, and mixtures thereof, wherein the heat-treated, ozonated vegetable oil composition comprises an aqueous phase and an oil phase; and
   c) separating at least a portion of the aqueous phase from the heat-treated, ozonated vegetable oil composition, wherein the at least a portion of the aqueous phase from the heat-treated, ozonated vegetable oil composition is an antimicrobial composition and/or virucidal disinfectant composition comprising a carboxylic acid chosen from a C1 carboxylic acid, a C2 carboxylic acid, a C3 carboxylic acid, a C4 carboxylic acid, and mixtures thereof.

2. The method of claim 1, wherein exposing a vegetable oil composition to ozone gas occurs while the vegetable oil composition is maintained at a temperature from greater than 0° C. to 60° C.

3. The method of claim 1, wherein exposing a vegetable oil composition to ozone gas occurs for time period from 1 minute to 20 hours.

4. The method of claim 1, wherein exposing a vegetable oil composition to ozone gas occurs via a batch and/or a continuous process.

5. The method of claim 1, wherein exposing a vegetable oil composition to ozone gas is chosen from sparging ozone gas into the vegetable oil composition, mixing ozone gas from a headspace into the vegetable oil composition, contacting ozone gas with the vegetable oil composition in a counter-current manner, and combinations thereof.

6. The method of claim 1, wherein exposing a vegetable oil composition to ozone gas occurs under a vacuum, at atmospheric pressure, or at a pressure greater than atmospheric pressure.

7. The method of claim 1, wherein exposing the ozonated vegetable oil composition to a temperature greater than 60° C. comprises exposing the ozonated vegetable oil composition to temperature from 80° C. to 100° C.

8. The method of claim 1, wherein exposing the ozonated vegetable oil composition to a temperature greater than 60° C. occurs for a time period from 1 minute to 48 hours.

9. The method of claim 1, further comprising a time period between steps "a" and "b," wherein the time period is less than 2 hours, and wherein ozone gas is not introduced into the ozonated vegetable oil composition during the time period.

10. The method of claim 1, wherein ozone gas is not introduced into the ozonated vegetable oil composition while exposing the ozonated vegetable oil composition to a temperature greater than 60° C.

11. The method of claim 1, wherein, after exposing the vegetable oil composition to ozone gas, washing the vegetable oil composition with an aqueous composition to form the ozonated vegetable oil composition comprising the aqueous phase and the oil phase.

12. The method of claim 1, wherein the vegetable oil composition is exposed to ozone gas while in contact with water.

13. The method of claim 1, further comprising adding an aqueous composition to the vegetable oil composition prior to exposing the vegetable oil composition to ozone gas, wherein, after adding an aqueous composition, the vegetable oil composition comprises a weight ratio of vegetable oil component to water in the range from 1:0.1 to 1:10.

14. The method of claim 1, further comprising washing the heat-treated, ozonated vegetable oil composition with an aqueous composition.

15. The method of claim 1, wherein the vegetable oil composition is derived from one or more process streams of a biorefinery, wherein the one or more process streams are chosen from whole stillage, thin stillage, syrup, oil emulsion, oil product, and combinations thereof.

16. The method of claim 1, wherein at least a portion of the oil phase from the heat-treated, ozonated vegetable oil composition is an antimicrobial composition and/or a virucidal disinfectant composition.

17. The method of claim 1, wherein the vegetable oil composition comprises a vegetable oil component chosen from corn oil, soybean oil, rape seed oil, sunflower oil, olive oil, castor bean oil, and combinations thereof.

18. The method of claim 1, wherein the ozonated vegetable oil composition has a concentration of ozone gas of one percent or less by weight of the ozonated vegetable oil composition while exposing the ozonated vegetable oil composition to a temperature greater than 60° C.

19. The method of claim 1, further comprising adding water to the vegetable oil composition prior to exposing the vegetable oil composition to ozone gas, wherein, after adding the water, the vegetable oil composition comprises a weight ratio of vegetable oil component to water in the range from 1:0.5 to 1:10.

20. A method of making one or more antimicrobial compositions and/or one or more virucidal disinfectant compositions, wherein the method comprises:
   a) exposing a vegetable oil composition to ozone gas to cause ozonolysis of one or more unsaturated fatty acids present in the vegetable oil composition, thereby forming an ozonated vegetable oil composition, wherein the ozonated vegetable oil composition comprises one or more ozonide compounds;
   b) exposing the ozonated vegetable oil composition to a temperature of 60° C. or greater while in contact with water to decompose one or more ozonide compounds via a decomposition reaction and form a heat-treated, ozonated vegetable oil composition, wherein the heat-treated, ozonated vegetable oil composition comprises an aqueous phase and an oil phase, and wherein at least step "b" does not occur in the presence of an exogenous amount of organic solvent that is a product of the decomposition reaction; and
   c) separating at least a portion of the aqueous phase from the heat-treated, ozonated vegetable oil composition, wherein the at least a portion of the aqueous phase from the heat-treated, ozonated vegetable oil composition is an antimicrobial composition and/or a virucidal disinfectant composition.

* * * * *